United States Patent
Serafini et al.

(10) Patent No.: US 8,389,716 B2
(45) Date of Patent: Mar. 5, 2013

(54) PROCESS FOR THE SYNTHESIS OF QUETIAPINE

(75) Inventors: Siro Serafini, Alte di Montecchio Maggiore (IT); Filippo Tomasi, Alte di Montecchio Maggiore (IT); Marco Galvagni, Alte di Montecchio Maggiore (IT)

(73) Assignee: F.I.S. Fabbrica Italiana Sintetici S.p.A., Alte di Montecchio Maggiore (IT)

( * ) Notice: Subject to any disclaimer, the term of this patent is extended or adjusted under 35 U.S.C. 154(b) by 207 days.

(21) Appl. No.: 13/001,713

(22) PCT Filed: Jan. 30, 2009

(86) PCT No.: PCT/EP2009/000610
§ 371 (c)(1), (2), (4) Date: Feb. 2, 2011

(87) PCT Pub. No.: WO2010/085976
PCT Pub. Date: Aug. 5, 2010

(65) Prior Publication Data
US 2011/0118460 A1     May 19, 2011

(51) Int. Cl.
*C07D 281/14* (2006.01)
(52) U.S. Cl. ........................................ 540/551
(58) Field of Classification Search .............. 540/551
See application file for complete search history.

(56) References Cited

FOREIGN PATENT DOCUMENTS
WO   WO 2005/026177 A1   3/2005
WO   WO 2006/073360 A1   7/2006

*Primary Examiner* — Brenda Coleman

(74) *Attorney, Agent, or Firm* — Dickstein Shapiro LLP

(57) ABSTRACT

The present invention relates to a process for the synthesis of quetiapine. In particular, a process is provided for the synthesis of quetiapine of formula (A) comprising reacting dibenzo[b,f][1,4]thiazepin-11(10H)-one, intermediate (I) with phosphorous oxychloride to give 11-chlorodibenzo[b,f][1,4]thiazepine, intermediate (II) wherein the said reaction of intermediate (I) to intermediate (II) is performed in an organic solvent in the presence of a mixture of an organic base together with an inorganic base.

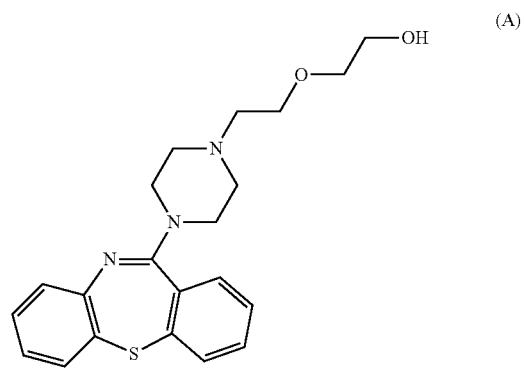

(A)

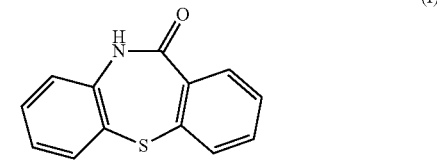

(I)

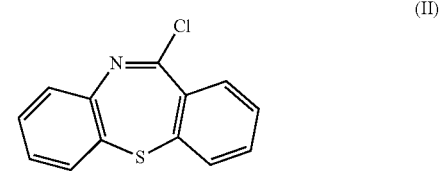

(II)

18 Claims, No Drawings

PROCESS FOR THE SYNTHESIS OF QUETIAPINE

The application is a national stage entry under 35 U.S.C. §371 of PCT/EP2009/000610, filed Jan. 30, 2009.

TECHNICAL FIELD OF THE INVENTION

The present invention relates to a process for the synthesis of quetiapine.

BACKGROUND ART

Quetiapine hemifumarate (ethanol, 2-[2-(4-dibenzo[b,f][1,4]thiazepin-11-yl-1-piperazinyl)ethoxy], (2E)-2-butenedioate (2:1) salt) is an antipsychotic drug deprived of undesired extrapyramidal side effects, that was developed by ICI and was launched on the market in 1997 under the name Seroquel.

Quetiapine is an achiral molecule of formula:

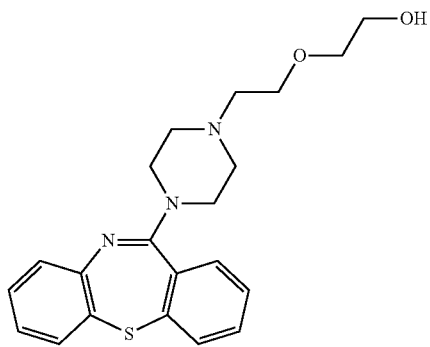 [SMILES: OCCOCCN1CCN(C2=Nc3ccccc3Sc3ccccc32)CC1]

Besides the hemifumarate salt, other salts are known in literature, such as dihydrochloride, maleate, fumarate, oxalate salts, as well as complexes with solvents.

In the art, quetiapine is synthesized starting from dibenzo[b,f][1,4]thiazepin-11(10H)-one (intermediate (I)

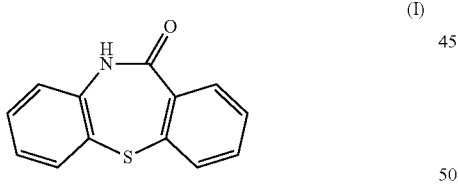

By reacting this intermediate with POCl$_3$, 11-chlorodibenzo[b,f][1,4]thiazepine (intermediate (II)) is obtained:

(II)

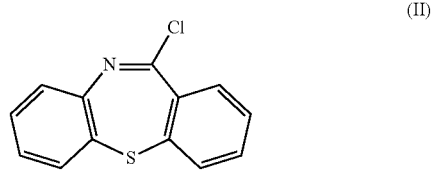 [SMILES: ClC1=Nc2ccccc2Sc2ccccc21]

This compound is then reacted with 1-(2-hydroxyethoxy)ethylpiperazine to give the title compound.

The formation of 11-chlorodibenzo[b,f][1,4]thiazepine (intermediate (II)) is a key step of the synthesis process.

EP 0 240 228 of AstraZeneca discloses the preparation of intermediate (II) by reaction of intermediate (I) with POCl$_3$ in the presence of N,N-disubstituted anilines. POCl$_3$ is used as a solvent.

US 2006/063927 of Chemagis describes the reaction of intermediate (I) with POCl$_3$ in an organic solvent at reflux and in the absence of a base.

WO 2006/117700 of Medichem relates to the preparation of intermediate (II) from intermediate (I) with POCl$_3$ in the presence of an organic amine, namely triethylamine, followed by decomposition of POCl$_3$ excess in situ.

WO 2006/135544 of Cambrex discloses the synthesis of intermediate (II) by reaction of intermediate (I) with POCl$_3$ in an organic solvent, namely toluene, in the presence of a trialkylamine such as triethylamine.

BRIEF DESCRIPTION OF THE INVENTION

It has now been surprisingly found that by reacting intermediate (II) with POCl$_3$ in the presence of a mixture of an organic amine and an inorganic amine, it is possible to obtain intermediate (II), 11-chlorodibenzo[b,f][1,4]thiazepine, with high yield, high purity and improved color characteristics.

DETAILED DESCRIPTION OF THE INVENTION

A process is provided for the preparation of intermediate (II), 11-chlorodibenzo[b,f][1,4]thiazepine:

(II)

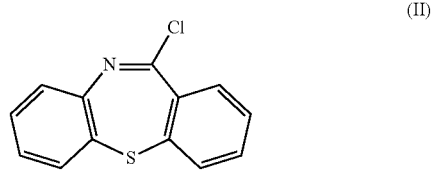 [SMILES: ClC1=Nc2ccccc2Sc2ccccc21]

comprising reacting the intermediate of formula (I):

(I)

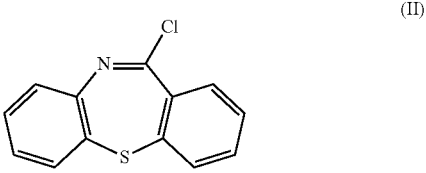

with phosphorous oxychloride POCl$_3$, in an organic solvent and in the presence of a mixture of an organic base together with an inorganic base.

The organic solvent can be selected among hydrocarbons, aromatic hydrocarbons, esters, ethers, chlorine solvents and the like. In a preferred embodiment, the solvent is an aromatic hydrocarbon, preferably toluene.

In an embodiment, the organic base can be a saturated or aromatic trialkylamine or a cyclic or polycyclic amine or an aromatic amine. In a preferred embodiment, the organic base is selected from N-methylmorpholine, triethylamine, dimethylaminopyridine, pyridine, N,N-diisopropylethylamine, dimethylaniline. More preferably, the organic base is N-methylmorpholine.

In an embodiment, the inorganic base can be a carbonate or hydrogencarbonate of an alkaline or alkaline-earth metal, or an hydroxide of an alkaline or alkaline-earth metal. In a preferred embodiment, the inorganic base is a carbonate of an alkaline metal, more preferably potassium carbonate.

The reaction can be conducted at reflux of the solvent for a time ranging from 3 to 8 hours, preferably between 4 and 6 hours.

The solvent can be used in an amount sufficient to keep intermediate (II) in solution at 0° C. If toluene is used as the solvent, such a volume amount ranges between 8 and 12 times the weight of intermediate (I), preferably about 10 times the weight of intermediate (I).

In an embodiment, phosphorous oxychloride $POCl_3$ is used in amounts ranging from 1.1 to 2.2 mol per mol of intermediate (I), preferably between 1.2 and 2 mol per mol of intermediate (I).

In an embodiment, the organic base is used in amounts ranging from 0.5 to 0.8 mol per mol of intermediate (I). In a preferred embodiment N-methylmorpholine is used in amounts ranging from 0.59 to 0.64 mol per mol of intermediate (I).

In an embodiment, the inorganic base is used in amounts ranging from 5 to 15% in weight with respect to the weight of intermediate (I). In a preferred embodiment, potassium carbonate is used in amounts ranging from 8 to 12% in weight with respect to the weight of intermediate (I).

In one embodiment, the reaction can be performed by dissolving or suspending in the organic solvent intermediate (I) and the inorganic base, then the organic base is added under stirring at room temperature. The reaction mixture is thus added dropwise with phosphorous oxychloride in a time ranging from 10 minutes to 1 hour, preferably about 30 minutes, then it is refluxed until completion of the reaction can be detected. Excess $POCl_3$ can be evaporated off under reduced pressure and the reaction mixture is worked-up.

Intermediate (II) as prepared according to the present invention has improved color characteristics, as it is clearer than the one obtained with the prior art methods. In addition, very high conversion (>99%) is achieved. These results are obtained thanks to the presence of the inorganic base together with the organic base. Experimental data have shown that while the elimination of the organic base does not allow the reaction to proceed, on the other hand the absence of the inorganic base lowers the conversion yield and furnishes a colored compound. A synergistic effect has thus been achieved by combining the organic base with the inorganic base according to the invention.

It is a further object of the present invention to provide a process for the synthesis of quetiapine or a salt thereof, the said process comprising preparing intermediate (II) as described above and a further step of converting such intermediate (II) into quetiapine by reaction with piperazinylethoxyethanol.

This reaction can be conducted in an organic solvent such as toluene. It is possible to use, after suitable work-up, the same toluene solution containing intermediate (II) obtained by the previous step of conversion of intermediate (I) into intermediate (II). The solvent is typically heated at reflux for several hours, typically more than 10 hours or more than 13 hours, until the reaction is complete, as monitored by HPLC analysis.

The reaction mixture is then cooled to room temperature and worked-up by addition of a strong base solution, such as 30% w/w solution of NaOH.

The resulting organic phase containing quetiapine is treated with an acidic aqueous solution such as a citric acid aqueous solution, washed with toluene and quetiapine free base is reconstituted by addition of a base such as a carbonate of an alkaline metal and extracted with an organic solvent.

Quetiapine as a free base is obtained by evaporating the solvent. A molar yield of 91-96% can be obtained.

Successively, a quetiapine salt can be obtained by treatment of the free base with a suitable pharmaceutically acceptable acid, such as fumaric acid, hydrochloric acid, maleic acid, oxalic acid and the like, according to the methods known in literature.

The invention will be now further described by means of illustrative examples that are not intended to limit the scope of protection as defined by the appended claims.

EXPERIMENTAL PART

Synthesis of intermediate (II),
11-chlorodibenzo[b,f][1,4]thiazepine

In a 2 l flask equipped with condenser, thermometer, mechanical stirring and under inert atmosphere, the following substances were charged:
 100 g of dibenzo[b,f][1,4]thiazepin-11(10H)-one (intermediate (I));
 10 g of potassium carbonate;
 1000 ml of toluene.

The mixture was stirred by keeping the temperature at 20-25° C. and 30 ml of N-methylmorpholine were added. While maintaining the reaction mixture under stirring at 20-25° C., 135 g of phosphorous oxychloride $POCl_3$ were added dropwise, then the organic suspension was heated at reflux for 4 hours and 30 minutes under stirring. After about 30 minutes at reflux, a yellowish solution appeared, afterward an oily dark residue was formed.

At the end of the prescribed time, the reaction mixture was cooled to 60-70° C. and excess $POCl_3$ together with part of the toluene (80-100 ml) were removed under vacuum, then further 100 ml of toluene were added and the reaction mixture was cooled to 0-5° C.

The toluene solution so obtained was added dropwise to a flask containing 100 ml of water, while keeping the temperature at 0-5° C.

The organic phase was separated and washed at 0-5° C. with a 10% w/w solution of sodium hydrogencarbonate. The organic phase was again separated, filtered over dicalite cake and dried, to give a toluene solution containing the title compound.

Synthesis of Quetiapine from Intermediate (II)

The toluene solution of intermediate (II) obtained as described above was added to 153.5 g of piperazinylethoxyethanol contained in a flask, then the reaction mixture was heated at reflux for 14-16 hours.

As the reaction was complete, the mixture was cooled to about 60° C., then 200 ml of water and 20 ml of 30% sodium hydroxide were added.

Under stirring, the reaction mixture was cooled to room temperature, then the organic phase was separated and washed with 200 ml of water and 5 ml of 30% sodium hydroxide.

After this operation, the organic phase was treated with 400 ml of water wherein citric acid monohydrate (36.1 g) was dissolved and the resulting aqueous phase was added with 200 ml of toluene and dropwise with 80 ml of hydrochloric acid. The aqueous phase was washed with toluene, then it was treated with a potassium carbonate aqueous solution and toluene.

The separated organic phase was decolored, filtered and the solvent was removed under vacuum, to obtain quetiapine free base with a molar yield of 92%.

The invention claimed is:

1. A process for the synthesis of quetiapine of formula:

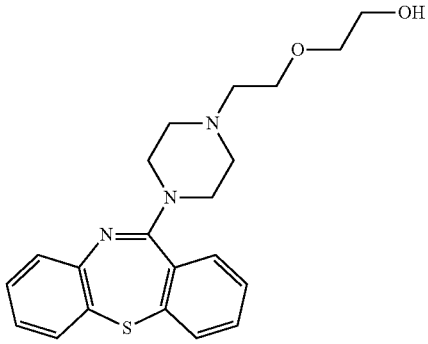 [SMILES: OCCOCCN1CCN(C2=Nc3ccccc3Sc3ccccc32)CC1]

comprising reacting dibenzo[b,f][1,4]thiazepin-11(10-H)-one, intermediate (I):

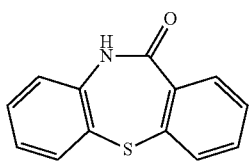

(I)

with phosphorous oxychloride POCl₃ to give 11-chlorodibenzo[b,f][1,4]thiazepine, intermediate (II):

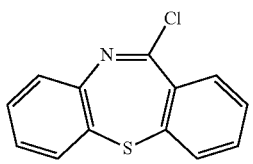

(II)

wherein the said reaction of intermediate (I) to intermediate (II) is performed in an organic solvent in the presence of a mixture of an organic base together with an inorganic base.

2. The process of claim 1, wherein the said organic solvent is selected among hydrocarbons, aromatic hydrocarbons, esters, ethers, chlorine solvents and the like.

3. The process of claim 2, wherein the solvent is toluene.

4. The process of claim 1, wherein the organic base is selected from a saturated or aromatic trialkylamine or a cyclic or polycyclic amine or an aromatic amine.

5. The process of claim 4, wherein the organic base is selected from N-methylmorpholine, triethylamine, dimethylaminopyridine, pyridine, N,N-diisopropylethylamine, dimethylaniline.

6. The process of claim 4, wherein the organic base is N-methylmorpholine.

7. The process of claim 1, wherein the inorganic base is selected from a carbonate or hydrogencarbonate of an alkaline or alkaline-earth metal or an hydroxide of an alkaline or alkaline-earth metal.

8. The process of claim 7, wherein the inorganic base is a carbonate of an alkaline metal or potassium carbonate.

9. The process of claim 1, wherein the reaction is conducted at reflux of the solvent for a time ranging from 3 to 8 hours or between 4 and 6 hours.

10. The process of claim 1, wherein the solvent is used in an amount sufficient to keep intermediate (II) in solution at 0° C.

11. The process of claim 10, wherein the solvent is toluene in a volume amount ranging from 8 to 12 times the weight of intermediate (I) or about 10 times the weight of intermediate (I).

12. The process of claim 1, wherein phosphorous oxychloride POCl₃ is used in amounts ranging from 1.1 to 2.2 mol per mol of intermediate (I), or between 1.2 and 2 mol per mol of intermediate (I).

13. The process of claim 1, wherein the organic base is used in amounts ranging from 0.5 to 0.8 mol per mol of intermediate (I).

14. The process of claim 13, wherein the organic base is N-methylmorpholine in amounts ranging from 0.59 to 0.64 mol per mol of intermediate (I).

15. The process of claim 1, wherein the inorganic base is used in amounts ranging from 5 to 15% in weight with respect to the weight of intermediate (I).

16. The process of claim 15, wherein the inorganic base is potassium carbonate in amounts ranging from 8 to 12% in weight with respect to the weight of intermediate (I).

17. The process of claim 1, wherein the reaction is performed by:
   dissolving or suspending in the organic solvent intermediate (I) and the inorganic base,
   adding the organic base under stirring at room temperature,
   adding dropwise to the reaction mixture phosphorous oxychloride POCl₃ in a time ranging from 10 minutes to 1 hour,
   refluxing the reaction mixture until completion of the reaction,
   evaporating off the excess of phosphorous oxychloride POCl₃.

18. The process of claim 1, further comprising a step of:
   converting intermediate (II) into quetiapine free base by reaction with piperazinylethoxyethanol in an organic solvent,
   optionally, converting quetiapine free base into a quetiapine salt by treatment with a pharmaceutically acceptable salifying acid.

* * * * *